United States Patent [19]

George, Jr.

[11] Patent Number: 4,482,865
[45] Date of Patent: Nov. 13, 1984

[54] APPARATUS FOR THE AUTOMATIC INDUCEMENT OF A MAGNETIC FIELD IN AN ELONGATED ARTICLE UNDER TEST

[75] Inventor: Kenneth E. George, Jr., McKeesport, Pa.

[73] Assignee: United States Steel Corporation, Pittsburgh, Pa.

[21] Appl. No.: 385,912

[22] Filed: Jun. 4, 1982

[51] Int. Cl.³ .................. G01N 27/84; G01R 33/12
[52] U.S. Cl. .................................. 324/263; 324/216; 324/262
[58] Field of Search ................... 324/214–216, 324/261–263, 226, 228, 207, 208; 361/143, 144

[56] References Cited

U.S. PATENT DOCUMENTS

| | | | |
|---|---|---|---|
| Re. 19,611 | 6/1935 | DeForest | 324/263 |
| 2,990,512 | 7/1961 | Gewartowski et al. | 324/216 |
| 3,271,663 | 9/1966 | Gewartowski et al. | 324/216 |
| 3,311,819 | 3/1967 | Miller | 324/226 |
| 3,939,404 | 2/1976 | Tait | 324/226 X |
| 4,041,379 | 8/1977 | Karlsson | 324/260 |
| 4,314,203 | 2/1982 | Haberlein | 324/262 |
| 4,339,714 | 7/1982 | Ellis | 324/262 X |

FOREIGN PATENT DOCUMENTS 340956  6/1972  U.S.S.R. .................. 324/263

*Primary Examiner*—Gerard R. Strecker
*Attorney, Agent, or Firm*—George D. Dickos

[57] ABSTRACT

An automatic overhead trolley-driven magnetizing system for inducing a residual magnetic field in seamless steel pipe in order to detect non-visual defects therein by the magnetic particle inspection method is described. The magnetizing system consists of a trolley-driven magnetizing unit which moves on an overhead runway until a retractable limit switch causes the unit to stop upon reaching the trailing end of the pipe, an electrical contact pad then lowers onto the surface of the pipe, and introduces a magnetizing current to the pipe sufficient to cause magnetic particles deposited on the pipe surface to indicate the location of defects in the pipe. The magnetizing system is arranged to remain remote from the manufacturing flow path of the workpiece until the magnetization thereof is required.

8 Claims, 6 Drawing Figures

FIG. 6

APPARATUS FOR THE AUTOMATIC INDUCEMENT OF A MAGNETIC FIELD IN AN ELONGATED ARTICLE UNDER TEST

DESCRIPTION OF THE INVENTION
BACKGROUND

The present invention relates to the magnetic inspection of magnetizable articles and, in particular, to a means for automatically inducing a magnetic field in an elongated metallic workpiece after which the workpiece is dusted with magnetic powder in order to locate defects therein by noting the orientation of the particles on the workpiece surface.

As is well known, if an article consisting of a magnetizable material is subjected to the action of a magnetizing force, lines of magnetic flux are set up in such an article. The paths taken by these lines of flux are in large part determined by both the degree of continuity and the homogeneity of the article. When discontinuities, cracks, flaws or inhomogeneities of any kind are present in a magnetized article, the lines of flux present therein are distorted by such defects. Accordingly, as is also known, if finely divided magnetic particles are deposited on the surface of a magnetized article containing a defect, the particles will, due to the stray lines of flux, be attracted predominantly to the surface of the article immediately above the defect, thus indicating the location of the defect.

This magnetic particle method of defect detection may be utilized as either a primary or secondary workpiece inspection means. When used as the primary inspection system, the magnetizing and inspection operations will often occur directly in the flow path of the manufacture of an article. When used as the secondary inspection system, the magnetic particle inspection will customarily occur following the primary inspection of the workpiece. It is contemplated that such a primary inspection may be accomplished by, e.g., a Non-Destructive Inspection (NDI) unit. Such a NDI unit may inspect the article by means of eddy currents induced in the article. When a defect is detected in the workpiece by the NDI unit, the work is automatically paint sprayed on the surface in the area of the defect. While most defects on the surface can be visually pinpointed with the aid of the paint spray marks, certain defects are not visible and necessitate further demarcation. In such an instance, a secondary, magnetic particle inspection means is useful, particularly in the embodiment provided herein.

As is apparent from the previous description of the process of magnetic particle flaw detection, the critical and most difficult step in the process is the magnetization of the article. Presently, many facilities effect the magnetization of the workpiece by the time-consuming operation of manually affixing electrical cables to the ends of the workpiece and passing a high amperage electrical current therethrough. Obviously, this is a most dangerous method of magnetization due to the direct human contact with the electrical current source.

Various apparatuses for accomplishing the magnetization of elongated articles have been developed. For example, the apparatuses disclosed in U.S. Pat. Nos. 3,271,663 and 2,990,512 issued to Gewartowski, et al, are directed to magnetic inspection means for billets. Each of these devices accomplishes the magnetization of the billet by a magnetizing means that abuts the ends of the billet. As such, the apparatuses of U.S. Pat. Nos. 3,271,663 and 2,990,512 require the transverse movement of the workpiece out of a straight-line flow path in order to accomplish the magnetization thereof. In fact, no known prior devices have accomplished the magnetization of an elongated workpiece automatically and without necessitating a deviation in the original manufacturing flow path of the work.

The subject invention is directed toward an improved means for rapidly and automatically magnetizing a workpiece which is to be inspected by the magnetic particle inspection method, without necessitating a deviation in the normal straight-line flow path of the workpiece through a manufacturing facility.

SUMMARY OF THE INVENTION

In accordance with the present invention, there is provided apparatus for the rapid automatic in-line magnetization of a workpiece, particularly so as to facilitate the magnetic particle inspection thereof. The present inspection means may be located immediately adjacent a Non-Destructive Inspection unit in the manufacturing flow path of the workpiece. If a workpiece does not require additional inspection, it passes directly through the herein provided apparatus in its usual manufacturing flow path. However, should a particular workpiece require additional inspection following the non-destructive inspection, a movable mechanical stop is activated at the distal end of the present inspection apparatus to halt the progress of the workpiece therethrough. An overhead runway means is provided on which rides a motorized carriage which supports the magnetizing unit proper. The magnetizing unit consists of a vertically retractable workpiece locating means which stops the carriage movement over the trailing end of the workpiece and an independently vertically retractable electrical contact pad which lowers into electrical contact with the workpiece upon reaching the trailing end thereof. The workpiece is provided to be supported on electrically insulated conveyor rolls. A source of magnetizing current is then provided to pass in the workpiece between the electrical contact pad and a second electrical contact means provided at the leading end of the workpiece. Following the magnetization of the workpiece, magnetic powder then can be deposited on the surface to indicate defects in the workpiece.

Accordingly, the present invention provides a rapid, effective means of automatically magnetizing a workpiece to enable the magnetic particle inspection thereof which does not require deviation in the typical flow path of such work or human contact with the magnetizing means.

These and other details, objects, and advantages of the invention will become apparent as the following description of the present preferred embodiment thereof proceeds.

BRIEF DESCRIPTION OF THE DRAWINGS

In the accompanying drawings, I have shown a present preferred embodiment of the invention wherein.

DETAILED DESCRIPTION OF THE INVENTION

Figure 1:
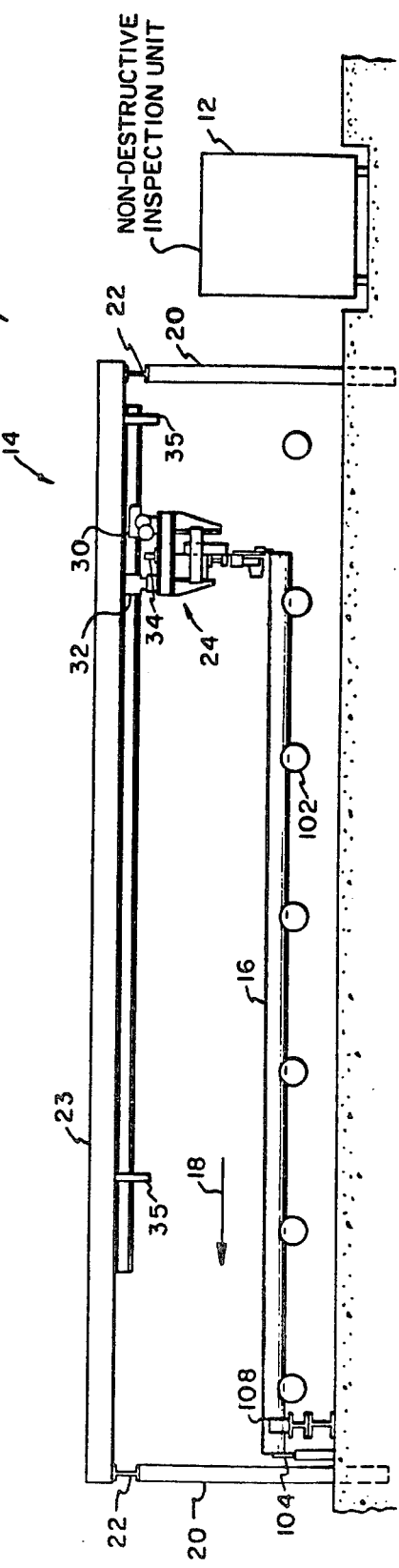
FIG. 1 is a side elevational view of the workpiece inspection system provided herein.

Referring now to the drawings wherein the showings are for purposes of illustrating the present preferred embodiment of the invention only and not for the purposes of limiting same, FIG. 1 shows a workpiece inspection system generally designated as 10 which includes both a Non-Destructive Inspection (NDI) unit 12 and an automatic magnetizing apparatus, generally designated 14, to facilitate the magnetic particle inspection of a workpiece 16. It is to be understood that the workpiece 16 referred to herein is to include any elongated magnetizable object such as, but not limited to, pipes, rods, bars, billets and the like.

More particularly and with reference again to FIG. 1, there is shown an automatic magnetizing apparatus 14 provided to magnetize a workpiece 16 which passes in a manufacturing flow path 18 therethrough following passage through the NDI unit 12. The magnetizing apparatus 14 includes a supporting structure which consists of four vertical posts 20, two at each end of apparatus 14, which support cross beams 22 which are affixed to the upper surfaces of posts 20 in transverse relation to the flow path 18 at either end of apparatus 14. An elevated runway 23 is provided above the flow path 18 and is affixed to and supported at each end by beams 22.

Figure 2:
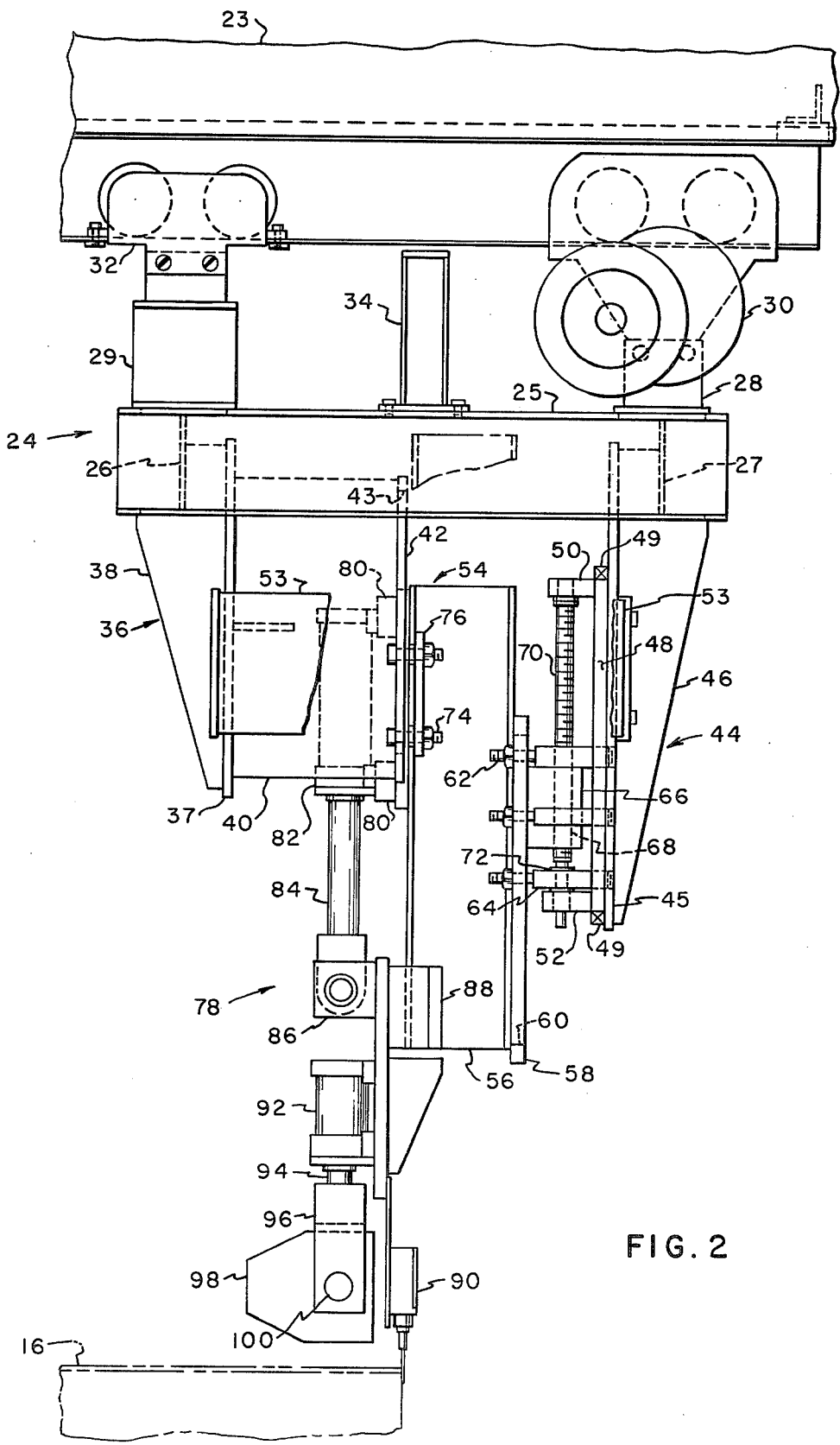
FIG. 2 is a side elevational view of the magnetizing unit according to the present invention.

As is illustrated in FIG. 2, provided for longitudinal movement along runway 23 is the magnetizing unit carriage means, generally designated as 24. The carriage assembly 24 includes four horizontal "I" beams, two longitudinal beams 25, leading lateral support beam 26 and trailing lateral support beam 27, said beams being weldedly affixed to one another and forming the shape of a rectangle. It is to be understood that the terms leading and trailing as used herein are intended to designate the ends which are furthest from and nearest to, respectively, the point of entry of workpiece 16 into apparatus 14. Rigidly affixed to the central upper surfaces of trailing lateral beam 27 is vertical member 28. A motorized trolley means 30 is operatively affixed to the top of the vertical frame member 28. An idler trolley 32 is operatively affixed to the top of the vertical frame member 29 disposed at the leading end of carriage 24. Trolleys 30 and 32 are configured to be supported by and ride along runway 23. A stop 34 traverses the central upper surfaces of longitudinal frame members 25 in order to prevent the carriage 24 from experiencing any excessive vertical displacement which may cause it to become disengaged from runway 23. Stops 35 are provided adjacent runway 23 to prevent carriage 24 from impacting beam 22 or running off of runway 23.

Figure 4:
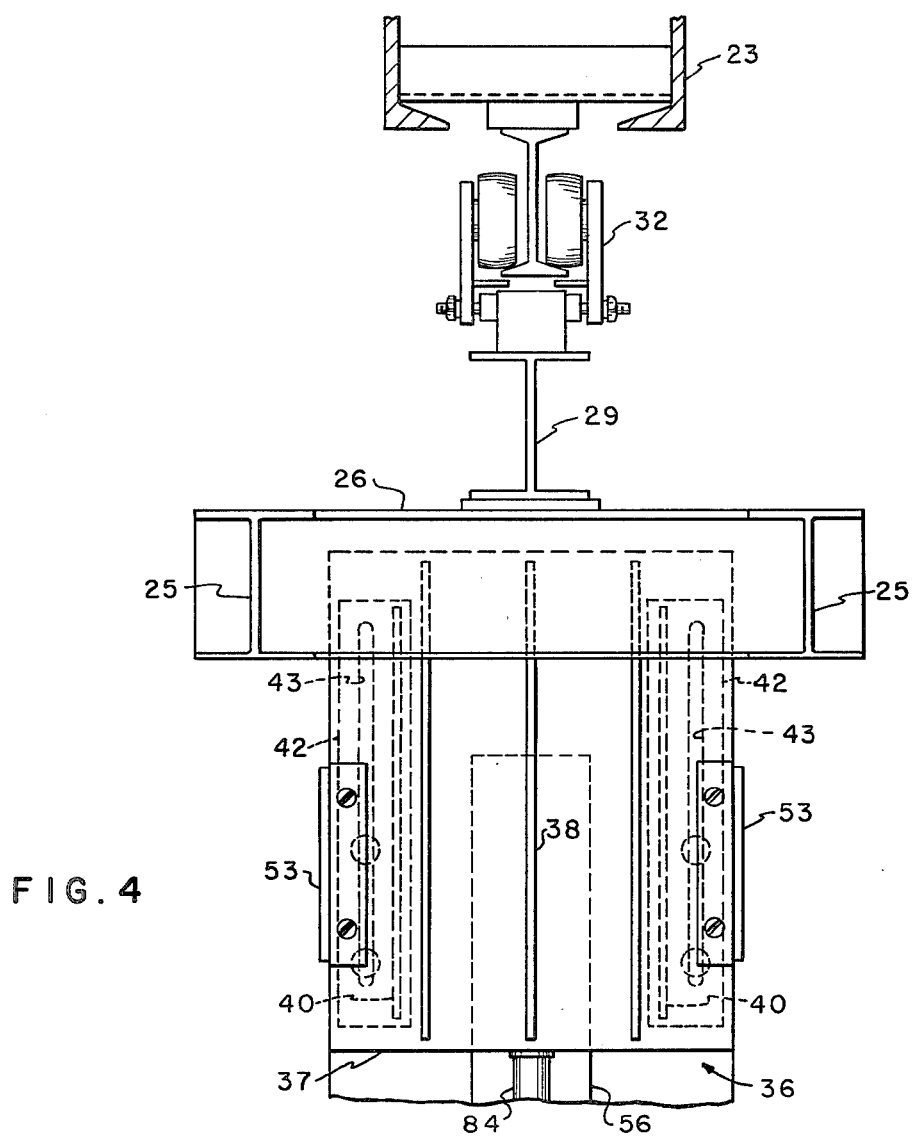
FIG. 4 is a front or leading end elevational view of the support structure of the herein provided apparatus.

As shown in FIGS. 2 and 4, the carriage assembly 24 also includes a leading vertical support member 36 which consists of a metallic plate 37 that is rigidly affixed to and depends from the leading lateral frame member 26 by means of ribs 38 rigidly affixed thereto. Extending longitudinally from the opposite sides of vertical support member 36 toward the trailing end of carriage 24 are vertical plates 40. Vertical members 42 which consist of bars having slots 43 are rigidly affixed to the trailing ends of vertical plates 40 in a configuration transverse to the direction of flow path 18. The trailing end of the carriage 24 includes a vertical support member 44 which consists of a vertical plate 45 that is rigidly affixed to and depends from the trailing lateral frame member 27 by means of ribs 46 welded thereto. Rigidly attached to the leading end of vertical member 44 is a parallel vertical plate which forms adjusting bracket 48. Shear blocks 49 are fixedly disposed on vertical plate 45 at the upper and lower surfaces of adjusting bracket 48 in order to provide additional support thereto. Configured to extend horizontally toward the leading edge of carriage 24 at the opposite corners of the top of adjusting bracket 48 are end plates 50. Extending horizontally toward the leading end of carriage 24 and weldedly affixed to the opposite lower corners of adjusting bracket 48 are apertured adjusting screw supports 52. In order to add additional rigidity to the carriage 24, side braces 53 comprising horizontal bars are rigidly affixed intermediate vertical support members 36 and 44 on each lateral side thereof.

Figure 3:
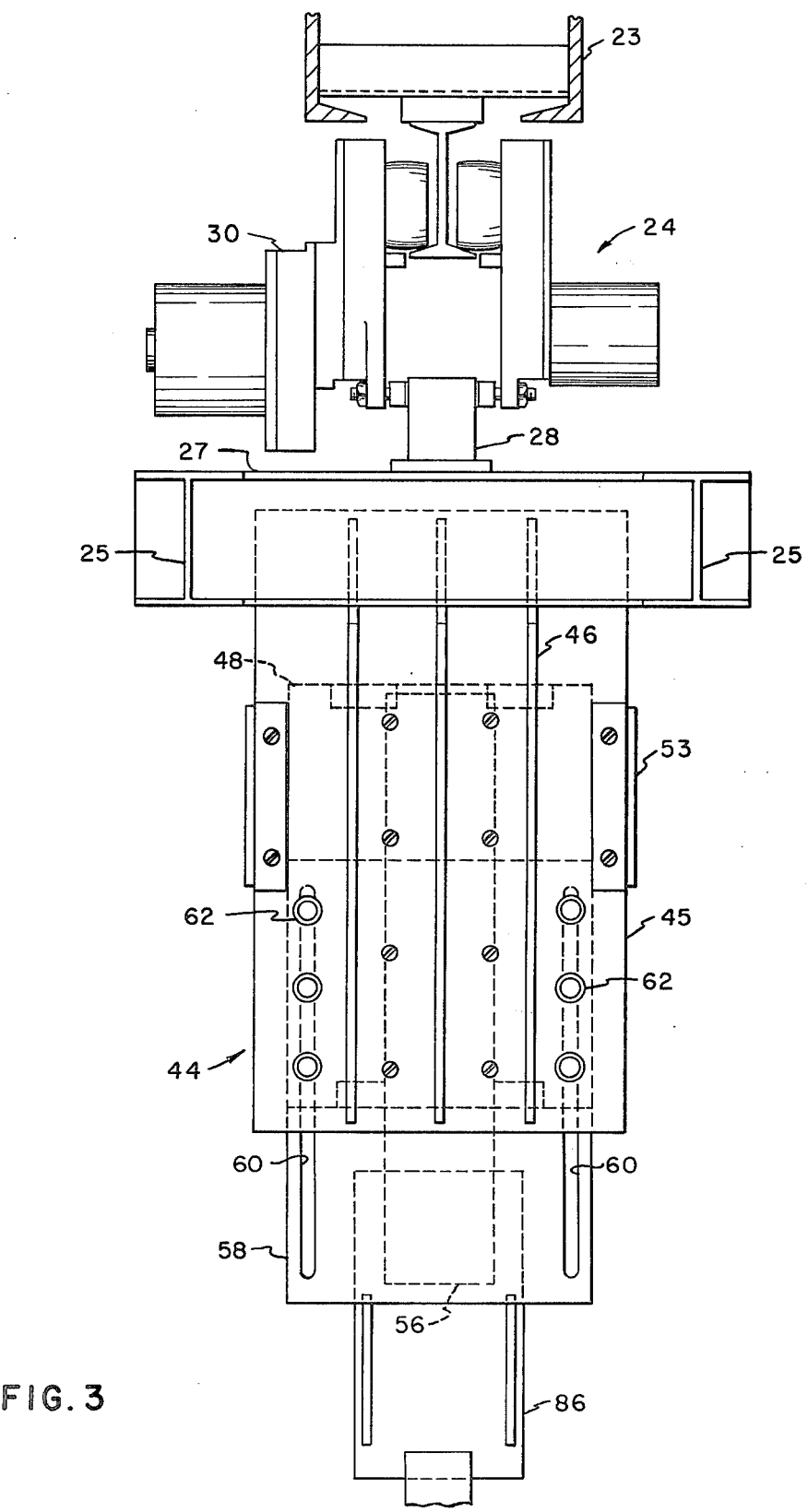
FIG. 3 is a rear or trailing end elevational view of the support structure of the herein provided apparatus.

Having fully described the carriage assembly 24, the means, generally designated 54 and shown in FIGS. 2 and 3, provided for the initial height adjustment of the magnetizing unit proper will now be disclosed. The height adjustment means 54 includes a vertical member 56, such as an "I"-beam, configured intermediate vertical members 42 and 48 with its web disposed along the longitudinal axis of the magnetizing apparatus 14. Firmly affixed to the flange at trailing end of member 56 is a vertical plate 58 which extends substantially across the width of carriage 24 and has vertical slots 60 extending along each vertical side thereof. The adjusting means 54 is supported in part by means of a plurality of bolts 62 which pass through slots 60, adjusting bracket 48 and vertical plate 45. Spacers 64 are provided to surround bolts 62 in order to assure proper spacing between vertical plate 58 and adjusting bracket 48. Height adjustment blocks 66 are configured to extend from the opposing lateral sides of vertical plate 58 toward adjusting bracket 48 and contain threaded apertures 68 therein. In order to vary the height of the magnetizing unit, to be described more fully herein, twin adjusting screws 70 are provided to be supported at their opposite ends by end plates 50 and supports 52. Further, adjusting screws 70 pass through and movably support height adjustment blocks 66 by means of threaded apertures 68. In order to assure the simultaneous adjustment of the screws 70, a chain and sprocket means shown generally as 72 is connected intermediate the screws 70 such that the turning of one screw 70, rotates the other screw 70 a similar amount. The height adjustment means 54 is supported at its leading end by means of bolts 74 which pass through vertical plates 76 which are weldedly affixed to the leading flange of member 56, and through the slots 43 in vertical members 42.

Having disclosed the supporting structure comprising the carriage 24 and the height adjustment means 54, the operative portion, generally designated 78 and shown in FIG. 2, of the magnetizing unit 14 will now be described. Rigidly affixed to the upper portion of the leading flange of vertical member 56 by means of supports 80 is the first vertically retractable support means 82. This retraction means 82 preferably consists of an air cylinder of sufficient stroke of piston 84 to cause the thereto attached workpiece locating means, fully described below, to be operative to locate the trailing end of workpiece 16 and to halt the progress of carriage 24 along runway 23 above said trailing end. As such, the housing of the air cylinder 82 is attached to support 56 with the piston 84 extending downwardly therefrom. Affixed to the lower terminous of the piston 84 is the cylinder bracket 86. The cylinder bracket 86 consists of a longitudinal member to which is affixed at the trailing end thereof a transverse vertical plate. To assure the completely vertical motion of piston 84, a guide means 88 attached to the trailing side of the cylinder bracket 86 is configured to operatively engage the leading flange of vertical member 56 so as to ride vertically thereon. Rigidly affixed to the trailing side of the lower end of cylinder bracket 86 is the workpiece locating means 90. Locating means 90 preferably consists of a downwardly extending limit switch, but it is to be understood that any position locating means, such as, for purposes of example only, a photo-electric location detector, may be substituted therefor. Locating means 90 is operatively connected to the control means for the motorized trolley 30, in a manner known to those skilled in the art, to halt the longitudinal progress of carriage 24 above the workpiece 16 upon locating the trailing end thereof.

As is also shown in FIG. 2, fixedly attached to the leading end of the vertical plate portion of cylinder bracket 86 is the second vertically retractable support means 92. This vertical retraction means 92, like the first vertical retraction means 82, preferably comprises an air cylinder. The second vertical retraction means 92 is also disposed in a downward orientation. Operatively affixed to the lower terminous of the piston 94 of the second vertical displacement means 92 is an electrically insulated support bracket 96. The primary magnetizing means 98 is operatively affixed to the bracket 96 by means of pin 100. Primary magnetizing means 98 preferably comprises a copper block fabricated into a contact pad. However, it is anticipated that any suitable means of establishing electrical contact with the workpiece 16 may be employed as the primary contact means 98.

Figure 5:
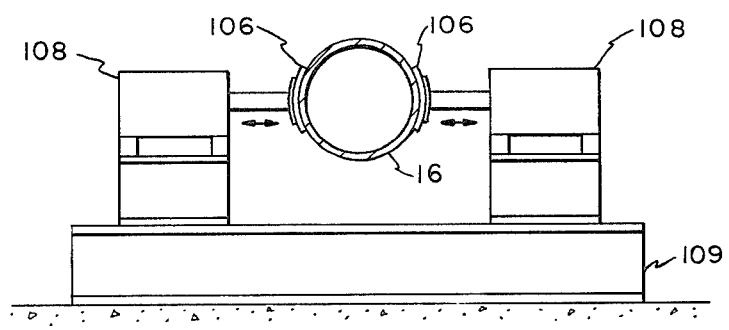
FIG. 5 is a rear elevational view of the secondary electrical contact means; and, FIG. 6 is a schematic diagram of the magnetizing circuit contemplated herein.

During the magnetizing operation, the workpiece is supported by electrically insulated conveyor rolls 102 shown in FIG. 1. Located adjacent and intermediate the vertical posts 20 at the leading end of the apparatus 14 is a selectively movable stopping means 104. Also located near the leading end of apparatus 14 and immediately adjacent the flow path 18 is the secondary electrical contact means 106, shown in FIG. 5, which consists of contact clamps which are electrically insulated from and movably supported by twin displacement means 108 such as air cylinders which rest on a common base 109. Means 108 is configured out of the flow path 18 so as to permit the displacement of second electrical contact means 106 between a position which is out of flow path 18 and allows the transverse movement of workpiece 16 and a position in electrical contact with workpiece 16.

Figure 6:
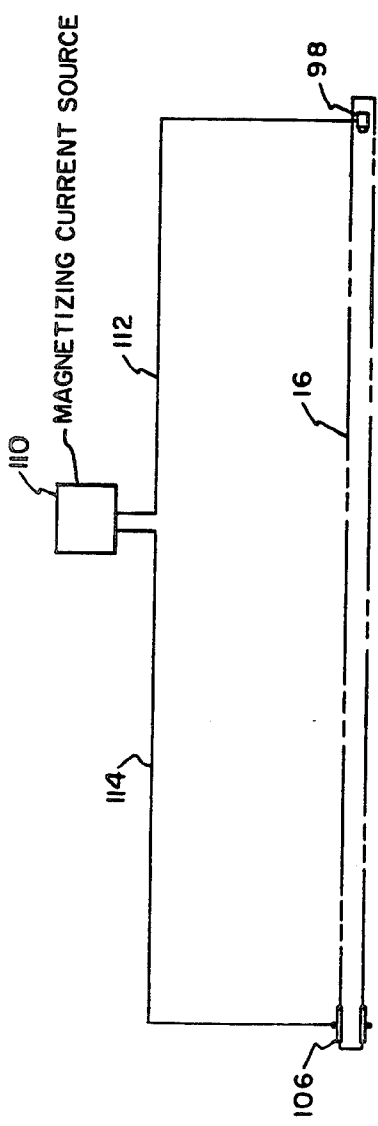

The magnetizing circuitry utilized herein is depicted in FIG. 6. The magnetizing current is provided by means of a source of current 110 such as a magnetizing power pack. This magnetizing current source 110 may consist of any source of low-voltage, high-amperage, full wave direct current suitable for magnetizing purposes. A suitable source of magnetizing current, by means of example only, is the Magnaflux Special CRQ-10 unit. The current source 110 preferably, but not necessarily, should be capable of a maximum current rating of 10,000 amperes. One output terminal of current source 110 is connected to a cable 112 which, in turn, is connected to contact pad 98 while the other terminal is connected via a cable 114 to the secondary electrical contact means 106. As such, when the circuit is complete and energized, the magnetizing current is provided to pass only from the current source 110, through cable 112 into contact pad 98, through the workpiece 16, into secondary electrical contact means 106, through cable 114 and back to the current source 110.

Prior to the operation of magnetizing unit 14, certain initial parameters are to be provided. First, the initial height of the locating means 90 and the contact pad 98 are to be set by adjusting the height of the vertical member 56. In order to position the initial height of the contact pad 98 to approximately two (2) inches above the surface of the workpiece 16 to be magnetized, the first vertical retraction means 82 must be energized thus lowering magnetizing means 98. Next, the bolts 62 and 74 are loosened, but not removed, thus enabling sliding movement of vertical member 56 along slots 60 and 43, respectively. The vertical member 56 is then displaced with respect to carriage 24 by means of the adjusting screws 70 which turn together due to chain and sprocket 72. Following the adjustment of contact pad 98 to approximately two (2) inches above the height of workpiece 16, the bolts 74 and 62 are tightened thereby locking the vertical member 56 in place.

Having described the mechanical apparatus which forms the magnetizing apparatus 14, the appropriate circuitry to automatically carry out the following operations is intended to be included herein. First, the carriage means 24 is moved to its start-up position longitudinally behind the anticipated location of the trailing end of workpiece 16 which, of course, is based on the length of the workpiece 16 to be inspected. Typically, the selection of one of three (3) start-up positions is sufficient to enable magnetizing unit 14 to magnetize a great variety of workpiece 16 lengths. The operation of the herein described apparatus is triggered by the results of the non-destructive inspection of the workpiece 16 by its passage through the NDI unit 12. A signal from the NDI unit 12 controls the movable stop 104 located at the leading end of the apparatus 14. If the pipe is free of all defects, the movable stop 104 will automatically lower, thus allowing the pipe to continue on the flow path 18 to the remainder of the manufacturing process.

If, however, the NDI unit 12 discovers a defect in the workpiece 16, the movable stop 104 will remain in an upright position thereby halting the progress of the workpiece 16 along the flow path 18 within the magnetizing apparatus 14. When a workpiece 16 having a defect comes in contact with the movable stop 104, the section of the workpiece conveying apparatus consisting of conveyor rolls 102 is automatically stopped thereby positioning the workpiece 16 correctly for the magnetizing operation. At this point, the air-powered movement means 108 of the secondary electrical contact means 106 automatically energizes thereby moving the contact elements 106 from their initial position out of the flow path 18 and into their second position in electrical contact with workpiece 16. Simultaneously, with the closing of the secondary electrical contact means 106 the motorized trolley 30 of the carriage means 24 will begin moving on runway 23 from its pre-selected starting position behind the trailing end of the workpiece 16 toward the leading end thereof. At the same time, the first vertically retractable means 82 will be energized and moved downward thus bringing workpiece locating means 90 into a path which will intersect the workpiece 16. It is to be noted that, at this time, the second vertically retractable means 92 will remain deenergized, that is, in its upmost position with the contact pad 98 prepositioned approximately two (2) inches above the workpiece 16. When the workpiece locating means 90 comes in contact with the trailing end of workpiece 16, two things happen simultaneously. First, the motorized trolley 30 of the carriage 24 will stop; and, second, the second vertical retraction means 92 will energize lowering the contact pad 98 into a position firmly in electrical contact with the surface of the workpiece 16 closely adjacent the trailing end thereof. When the secondary electrical contact means 106 and the contact pad 98 are in firm contact with the workpiece 16, the automatically controlled magnetizing current supply 110 causes the magnetizing current to flow through workpiece 16 thereby producing a residual magnetic field throughout the entire length of the workpiece 16. Following the magnetization of the workpiece 16, the following events occur simultaneously. First, the stopping means 104 will be retracted to a position out of the flow path 18. Second, the airpowered movement means 108 will cause the secondary electrical contact means 106 to return to their initial position out of the flowpath 18. Third, the first and second vertical retraction means 82 and 92, respectively, both deenergize thus allowing the now magnetized workpiece to be removed from the conveyor rolls 102 to the appropriate manufacturing location, for example transverse to the apparatus 14, for the application of the magnetic powder. As the next workpiece passes through the NDI unit 12, the carriage means 24 will be returning to its preselected starting position. The magnetizing unit 14 is now ready to repeat its magnetizing function. It is contemplated that the entire locating and magnetizing cycle may be completed in a matter of ten (10) seconds.

It will be understood that various changes in the details, materials and arrangements of parts which have been herein described and illustrated in order to explain the nature of the invention may be made by those skilled in the art within the principle and scope of the invention as expressed in the appended claims.

What is claimed is:

1. Apparatus for magnetizing an elongated magnetizable workpiece which passes in a longitudinal flow path through said apparatus comprising:
   (a) electrically insulated workpiece support means adapted to support said workpiece along a portion of said flow path;
   (b) primary support means including a rail member positioned above and parallel to the axis of said workpiece;
   (c) a carriage adapted to travel along said rail member between a first position remote from said workpiece and a second position above one end of said workpiece;
   (d) electric drive means operatively connected to said carriage to drive said carriage between said first and second positions;
   (e) workpiece locating means in electrical contact with said electric drive means, said workpiece locating means being effective to generate a signal to halt the movement of said carriage along said rail member when said carriage reaches said second position;
   (f) first vertically displaceable support means affixed to said carriage, said vertically displaceable support means supporting said workpiece locating means and being effective to displace said workpiece locating means between one position effective to locate said one end of said workpiece and another position out of said flow path;
   (g) a first electrical contact means;
   (h) second vertically displaceable support means affixed to said first vertically displaceable support means, said second vertically displaceable support means supporting said first electrical contact means and being effective to displace said first electrical contact means between a position in operative contact with said workpiece and another position out of said flow path;
   (i) second electrical contact means arranged with respect to the other end of said workpiece for movement between a position in operative contact with said workpiece and another position out of said flow path; and,
   (j) source of magnetizing current adapted to cause a magnetizing current to pass in said workpiece between said first and second electrical contact means when each is in its respective electrical contact position.

2. Apparatus of claim 1 in which said workpiece locating means comprises a limit switch.

3. Apparatus of claim 2 in which said first and second vertically displaceable support means each comprise a fluid motor.

4. Apparatus of claim 3 further comprising a selectively movable stopping means effective to stop the progress of said workpiece along said flow path when said workpiece is supported by said electrically insulated workpiece support means.

5. Apparatus of claim 4 in which said one end of said workpiece is the trailing end of said workpiece.

6. Apparatus of claim 5 in which said workpiece supporting means comprises a plurality of electrically insulated conveyor rolls.

7. Apparatus of claim 6 further comprising an adjustable support member affixed to said carriage and arranged to support said first retractable support means, said adjustable support member being adapted to provide for the adjustment of the position of said first retractable support means with respect to said carriage.

8. Apparatus of claim 7 in which said carriage comprises:
   (a) a horizontal framework;
   (b) a first vertical frame member affixed to one end of the upper surface of said horizontal framework, said first vertical frame member supporting said electric drive means;
   (c) second vertical frame member affixed to the other end of the upper surface of said horizontal framework; and,
   (d) an idler trolley operatively affixed to said second vertical member and configured to operably engage said rail member.

* * * * *